United States Patent
Horst et al.

(10) Patent No.: US 12,246,149 B2
(45) Date of Patent: Mar. 11, 2025

(54) CATHETER INSERTION APPARATUS WITH CONTINUOUS VISIBLE FLASHBACK

(71) Applicant: TELEFLEX MEDICAL INCORPORATED, Morrisville, NC (US)

(72) Inventors: Benjamin Horst, Lititz, PA (US); Mark Spinka, Jenkintown, PA (US); Jeffrey Kuehn, Schuylkill Haven, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 257 days.

(21) Appl. No.: 17/339,296

(22) Filed: Jun. 4, 2021

(65) Prior Publication Data
US 2021/0290913 A1    Sep. 23, 2021

Related U.S. Application Data

(63) Continuation of application No. PCT/US2020/027463, filed on Apr. 9, 2020.
(Continued)

(51) Int. Cl.
*A61M 25/06* (2006.01)
*A61M 25/02* (2006.01)
(Continued)

(52) U.S. Cl.
CPC ........ *A61M 25/0693* (2013.01); *A61M 25/09* (2013.01); *A61M 25/0015* (2013.01);
(Continued)

(58) Field of Classification Search
CPC ............ A61M 25/09; A61M 25/09041; A61M 25/0693; A61M 25/0606; A61M 25/0169;
(Continued)

(56) References Cited

U.S. PATENT DOCUMENTS 4,068,659 A * 1/1978 Moorehead ......... A61M 25/065
604/523
4,417,886 A * 11/1983 Frankhouser ..... A61M 25/0606
604/528
(Continued)

FOREIGN PATENT DOCUMENTS

CN     208611481 U    3/2019
JP     01-299567 A    12/1989
(Continued)

OTHER PUBLICATIONS

International Search Report for PCT/US2020/027463, mail date Jun. 23, 2020, 3 pages.

*Primary Examiner* — William R Carpenter
*Assistant Examiner* — Robert F Allen
(74) *Attorney, Agent, or Firm* — BakerHostetler

(57) ABSTRACT

The present disclosure relates to a catheter insertion apparatus including a hollow needle body connected to a needle hub, and a catheter that removably fits over the needle body. The needle body has a sharp distal needle tip for piercing a blood vessel wall. An internal flow passage of the needle hub is in fluid communication with the hollow needle body. An elongated housing is connected to the needle hub and includes a lumen in fluid communication with the internal flow passage of the needle hub. An integrated guide assembly is slidably mounted to the housing and is operable to move between a retracted position and an extended position. A flashback chamber is operable to receive a continuous flow of blood before, during, and after movement of the guide assembly between its retracted and extended positions. A safety guard may provide protection from the sharp needle tip.

19 Claims, 11 Drawing Sheets

Related U.S. Application Data

(60) Provisional application No. 62/833,477, filed on Apr. 12, 2019.

(51) Int. Cl.
*A61M 25/09* (2006.01)
*A61M 39/02* (2006.01)
*A61M 25/00* (2006.01)
*A61M 25/01* (2006.01)
*A61M 25/10* (2013.01)

(52) U.S. Cl.
CPC ..... *A61M 25/0169* (2013.01); *A61M 25/0172* (2013.01); *A61M 2025/0293* (2013.01); *A61M 25/0618* (2013.01); *A61M 25/0631* (2013.01); *A61M 25/065* (2013.01); *A61M 2025/09116* (2013.01); *A61M 2025/1056* (2013.01); *A61M 2039/0235* (2013.01)

(58) Field of Classification Search
CPC ...... A61M 25/0172; A61M 2025/0293; A61M 2025/1056; A61M 2039/0235; A61M 25/0015; A61M 25/065
See application file for complete search history.

(56) References Cited

U.S. PATENT DOCUMENTS

| | | | |
|---|---|---|---|
| 4,525,157 A * | 6/1985 | Vaillancourt | A61M 25/0111 604/165.01 |
| 4,652,256 A | 3/1987 | Vaillancourt | |
| 4,772,264 A | 9/1988 | Cragg | |
| 4,863,431 A * | 9/1989 | Vaillancourt | A61M 25/065 604/168.01 |
| 4,894,052 A | 1/1990 | Crawford | |
| 4,908,021 A | 3/1990 | McFarlane | |
| 4,908,201 A | 3/1990 | Cabanaw | |
| 4,935,008 A | 6/1990 | Lewis, Jr. | |
| 4,961,729 A | 10/1990 | Vaillancourt | |
| 5,116,323 A | 5/1992 | Kreuzer et al. | |
| 5,120,319 A | 6/1992 | Van Heugten et al. | |
| 5,137,288 A * | 8/1992 | Starkey | A61M 25/09 279/42 |
| 5,171,218 A | 12/1992 | Fonger et al. | |
| 5,246,426 A * | 9/1993 | Lewis | A61M 25/0693 604/168.01 |
| 5,257,979 A | 11/1993 | Jagpal | |
| 5,295,970 A | 3/1994 | Clinton et al. | |
| 5,330,433 A | 7/1994 | Fonger et al. | |
| 5,439,449 A | 8/1995 | Mapes et al. | |
| 5,575,777 A | 11/1996 | Cover et al. | |
| 5,690,619 A | 11/1997 | Erskine | |
| 5,695,479 A | 12/1997 | Jagpal | |
| 5,700,250 A | 12/1997 | Erskine | |
| 5,702,367 A | 12/1997 | Cover et al. | |
| 5,704,914 A * | 1/1998 | Stocking | A61M 25/0631 604/195 |
| 5,766,151 A | 6/1998 | Valley et al. | |
| 5,820,596 A | 10/1998 | Rosen et al. | |
| 5,980,492 A | 11/1999 | Rosen et al. | |
| 5,984,895 A | 11/1999 | Padilla et al. | |
| 6,197,001 B1 | 3/2001 | Wilson et al. | |
| 6,261,263 B1 | 7/2001 | Huet et al. | |
| 6,277,100 B1 | 8/2001 | Raulerson et al. | |
| 6,280,419 B1 | 8/2001 | Vojtasek | |
| 6,524,277 B1 | 2/2003 | Chang | |
| 6,533,759 B1 | 3/2003 | Watson et al. | |
| 6,533,760 B2 | 3/2003 | Leong | |
| 6,547,762 B1 | 4/2003 | Botich et al. | |
| 6,579,264 B1 | 6/2003 | Rossi | |
| 6,582,402 B1 | 6/2003 | Erskine | |
| 6,786,875 B2 | 9/2004 | Barker et al. | |
| 7,153,276 B2 | 12/2006 | Barker et al. | |
| 7,261,703 B2 | 8/2007 | Lampropoulos et al. | |
| 7,753,887 B2 | 7/2010 | Botich et al. | |
| 7,833,201 B2 | 11/2010 | Carlyon et al. | |
| 8,105,286 B2 | 1/2012 | Anderson et al. | |
| 8,412,300 B2 | 4/2013 | Sonderegger | |
| 8,540,750 B2 | 9/2013 | Tegels | |
| 8,585,651 B2 | 11/2013 | Asai | |
| 8,657,790 B2 | 2/2014 | Tal et al. | |
| 8,672,888 B2 | 3/2014 | Tal | |
| 8,728,035 B2 | 5/2014 | Warring et al. | |
| 9,138,252 B2 | 9/2015 | Bierman et al. | |
| 9,522,254 B2 | 12/2016 | Belson | |
| 9,566,087 B2 | 2/2017 | Bierman et al. | |
| 9,757,540 B2 | 9/2017 | Belson | |
| 9,764,117 B2 | 9/2017 | Bierman et al. | |
| 9,861,792 B2 | 1/2018 | Hall et al. | |
| 9,872,971 B2 | 1/2018 | Blanchard | |
| 9,884,169 B2 | 2/2018 | Bierman et al. | |
| 9,950,139 B2 | 4/2018 | Blanchard et al. | |
| 10,010,343 B2 | 7/2018 | Bierman et al. | |
| 10,232,146 B2 | 3/2019 | Braithwaite et al. | |
| 2004/0215146 A1 * | 10/2004 | Lampropoulos | A61B 5/15003 604/168.01 |
| 2005/0075606 A1 | 4/2005 | Botich et al. | |
| 2007/0073222 A1 * | 3/2007 | Lilley, Jr. | A61M 25/0618 604/110 |
| 2007/0191777 A1 | 8/2007 | King | |
| 2008/0262430 A1 * | 10/2008 | Anderson | A61M 25/09 604/165.01 |
| 2010/0179484 A1 | 7/2010 | Carrez et al. | |
| 2010/0204553 A1 | 8/2010 | Sonderegger | |
| 2011/0054406 A1 | 3/2011 | McKinnon | |
| 2011/0218496 A1 | 9/2011 | Bierman | |
| 2013/0338607 A1 * | 12/2013 | Paspa | A61B 90/05 604/533 |
| 2014/0214005 A1 * | 7/2014 | Belson | A61M 25/0606 604/510 |
| 2014/0257359 A1 | 9/2014 | Tegels et al. | |
| 2015/0051584 A1 * | 2/2015 | Korkuch | A61M 25/0606 604/95.01 |
| 2016/0067453 A1 | 3/2016 | Braithwaite et al. | |
| 2016/0175563 A1 | 6/2016 | Woehr et al. | |
| 2016/0256667 A1 * | 9/2016 | Ribelin | A61M 25/09041 |
| 2016/0331938 A1 * | 11/2016 | Blanchard | A61M 25/0618 |
| 2018/0071509 A1 * | 3/2018 | Tran | A61M 25/0097 |
| 2018/0117283 A1 | 5/2018 | Letang et al. | |
| 2018/0133438 A1 * | 5/2018 | Hulvershorn | A61M 25/0113 |
| 2018/0207406 A1 * | 7/2018 | Ishida | A61M 25/0631 |
| 2018/0229004 A1 * | 8/2018 | Blanchard | A61M 25/0618 |
| 2018/0280626 A1 | 10/2018 | Branson et al. | |
| 2018/0296799 A1 | 10/2018 | Horst et al. | |
| 2020/0001051 A1 | 1/2020 | Huang et al. | |
| 2021/0183436 A1 | 6/2021 | Chhabra et al. | |

FOREIGN PATENT DOCUMENTS

| | | |
|---|---|---|
| JP | 07-507945 A | 9/1995 |
| JP | 2016-530934 A | 10/2016 |
| WO | 2009/142208 A1 | 11/2009 |
| WO | 2015/168655 A2 | 11/2015 |
| WO | 2021183436 A1 | 9/2021 |

* cited by examiner

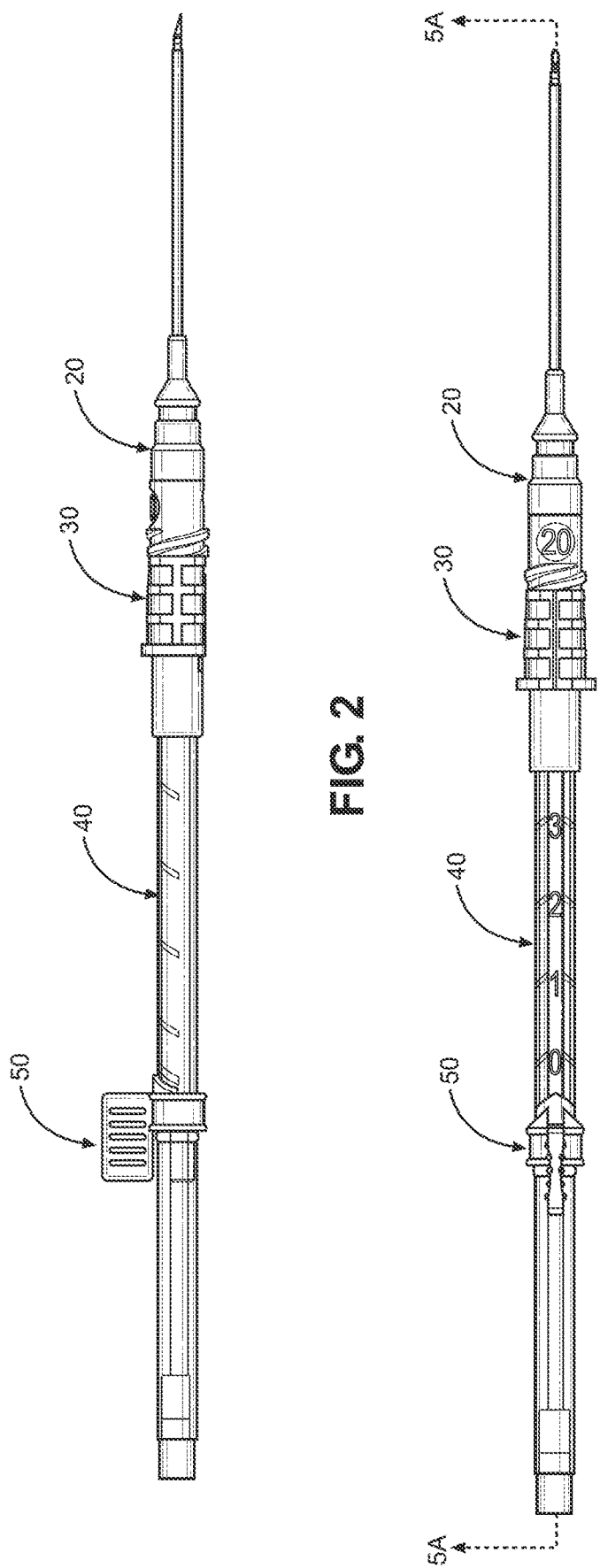

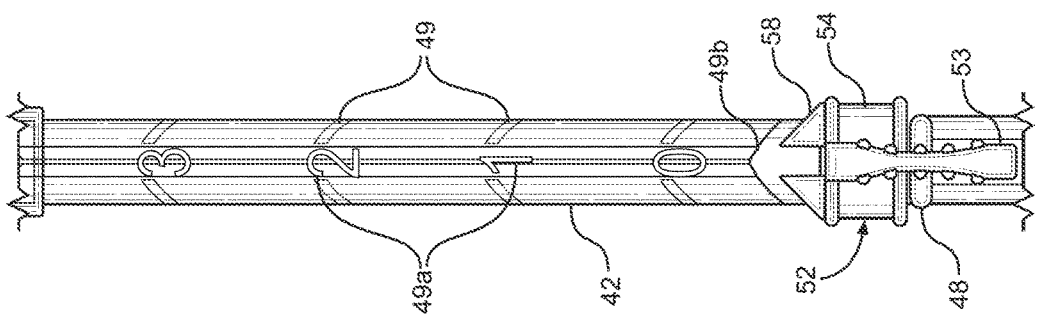
FIG. 9
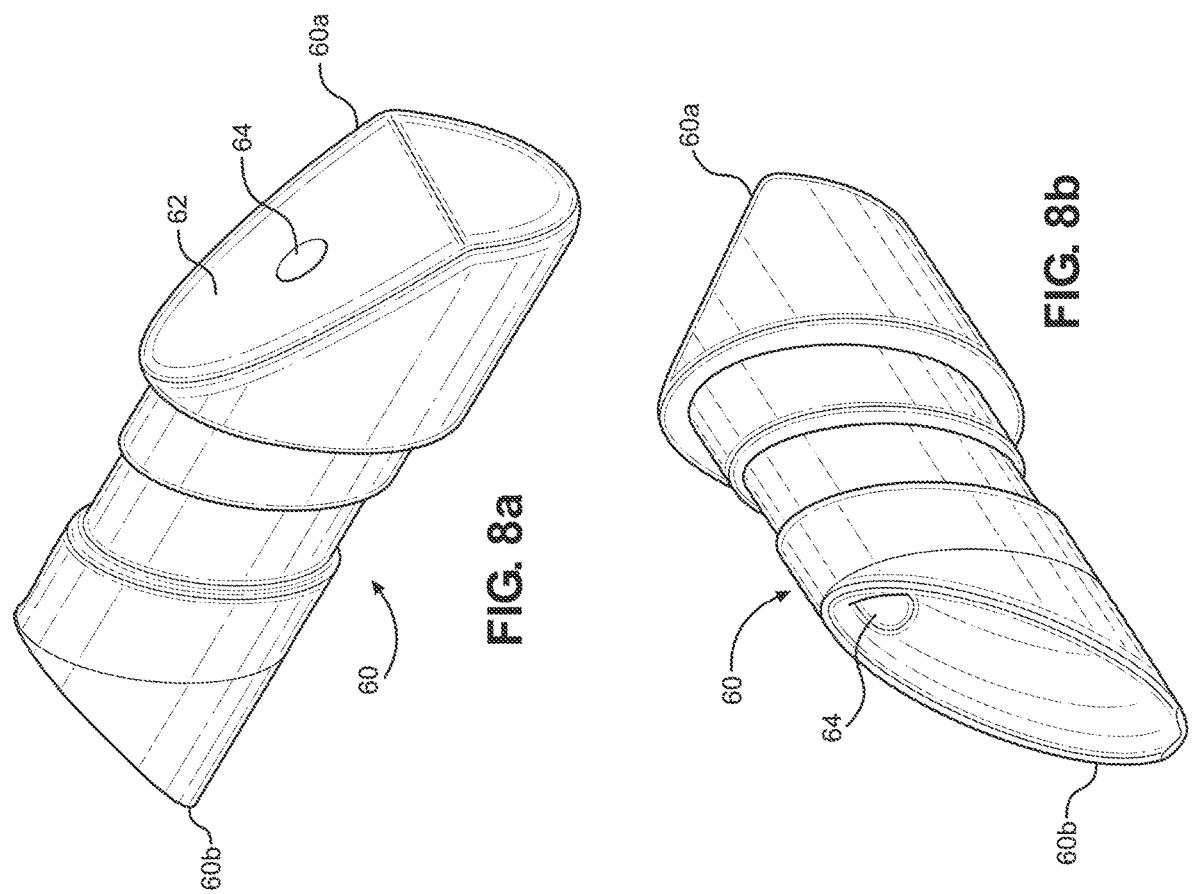
FIG. 8a
FIG. 8b

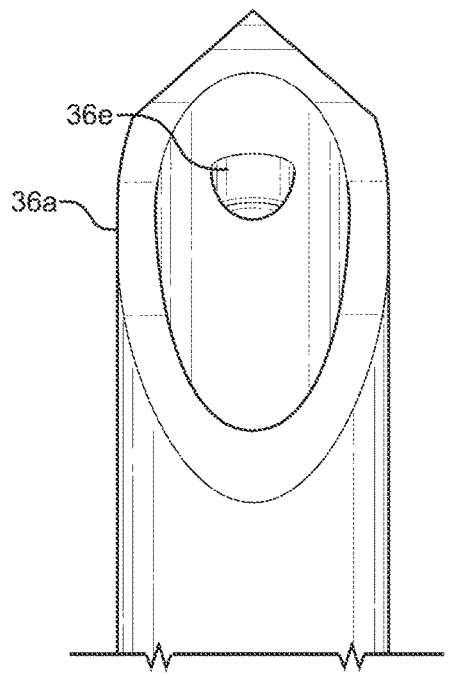 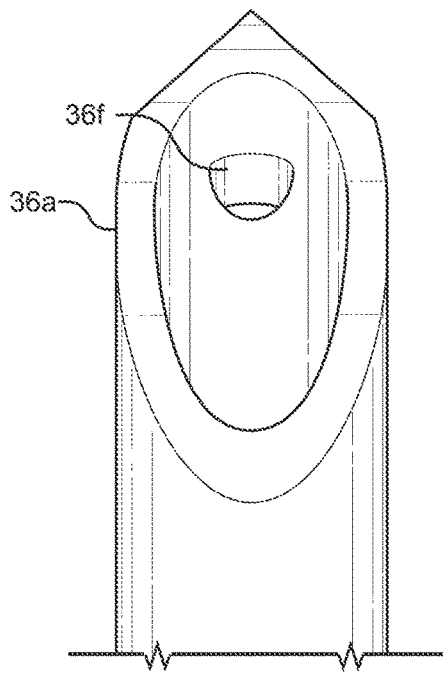
FIG. 12A　　　　　　　　FIG. 12B
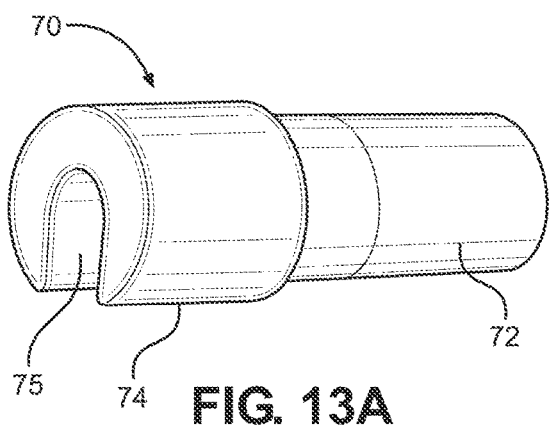 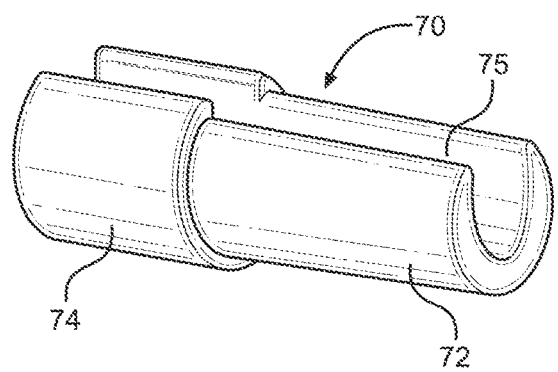
FIG. 13A　　　　　　　　FIG. 13B
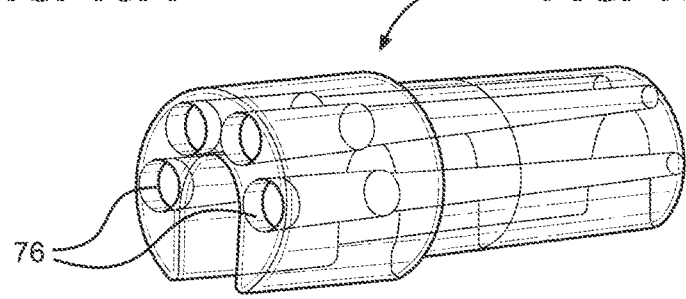
FIG. 13C

CATHETER INSERTION APPARATUS WITH CONTINUOUS VISIBLE FLASHBACK

CROSS-REFERENCE TO RELATED APPLICATION

This application is a continuation of International Application PCT/US2020/027463, filed on Apr. 9, 2020 and published as WO 2020/210488, which claims the benefit of U.S. Provisional Patent Application No. 62/833,477, filed on Apr. 12, 2019, the disclosures of which are hereby incorporated by reference in their entirety.

FIELD OF THE INVENTION

The present disclosure generally relates to a catheter insertion apparatus, and more particularly, to an integrated over-the-needle catheter insertion apparatus operable to provide continuous blood flash visibility during catheterization.

BACKGROUND

Catheters are commonly used to remove fluids from blood vessels of a patient, or introduce fluids into blood vessels, for a variety of medical procedures. For instance, radial artery catheterization may be performed to provide access to the arterial system via the radial artery for monitoring blood pressure and withdrawing blood. Catheters are often inserted into the vasculature via an integrated catheter insertion device. In a typical catheterization procedure, for instance, in order to insert a catheter in a vessel, the vessel access is first performed by using a long hollow needle to pierce the vessel wall. A guidewire is then passed through the needle and into the vessel. The guidewire acts as a track for the catheter to pass over to reach a target location within the vessel. A catheter is finally passed over the guidewire to the target location in the vasculature of the patient. With the catheter in place, the needle and the guidewire are removed, leaving only the catheter within the vessel. Fluids may then be introduced into, or removed from, the vessel through the catheter by connecting a fluid source or aspiration device to the catheter hub.

Conventional catheterization devices include a means for the practitioner to visualize blood flash for indicating when the tip of the needle has entered the vasculature during vessel puncture. Some known catheterization devices offer the ability for users to visualize blood flash in a wire advancement tube during vessel puncture after the pressurized vessel, such as an artery, is punctured which causes blood to flow through the internal diameter of the needle and subsequently flow out of an exit location at or near the back of the needle and into the wire tube that is located proximal to the catheter body portion of the catheterization device. These devices allow the practitioner to re-confirm vessel puncture if needed, since the blood flash can start, stop, and re-start if the distal needle tip enters, exits, and re-enters, respectively, the vessel during insertion. However, such devices do not permit (1) blood flash that is visible through the catheter body, and (2) blood flash in the device (i.e. the wire tube) during and after wire advancement.

Rather, the blood flash in conventional catheter insertion devices stops during and after the subsequent wire advancement step because the wire occupies too much of the volume within the needle, thus reducing flow. Moreover, the wires on conventional devices cannot start distal to the needle flash exit location without also taking up too much volume and causing blood flash flow to be reduced. Therefore, the wires must start proximal to the blood flash exit location near the back of the needle and thus the first significant portion of wire advancement results in the wire traveling from the back of the needle (proximal to the catheter body), through the catheter, to the tip of the needle (distal to the catheter body) before the wire is advanced into the vessel, which is also known as the "dead length" for wire advancement (i.e., advancement that moves the tip of the wire closer to the needle tip before the wire is advanced out of the needle). Such wire dead length is a common drawback in conventional devices, as it extends the catheterization procedure by causing a significant length of time between when flash is observed and when the wire is advanced into the vessel. During this time, continuous visible blood flash (and therefore information about the needle tip location) is not available in conventional devices.

Other conventional catheterization devices offer the ability for users to visualize blood flash during vessel puncture through a transparent, or partially translucent, catheter as the blood enters the small volume of space between the inside of the hollow catheter and the outside of the hollow needle. These devices show flash through the catheter when it enters into this small volume of space, but in practice the flash is considered once-and-done since such devices do not offer the ability for flash to re-start after it is first observed and very quickly fills this small volume of space. This aspect makes it difficult for the practitioner to recover an insertion in which the needle tip becomes misaligned with the vessel or passes through the vessel.

Thus, conventional catheterization devices do not permit: 1) blood flash visible through the catheter body, and/or 2) blood flash in the device (i.e., the wire tube or the like) during and after wire advancement. Therefore, a need exists for a novel catheter insertion device that allows for continuous visible blood flashback during insertion of a catheter into the vasculature of a patient. More particularly, there exists a need for a catheter insertion apparatus that offers the ability to visualize flash through the catheter and flash in the device (i.e., the wire tube or the like) (which also includes the ability to re-confirm flash in wire tube or the like), and also offer the ability to visualize flash during and after wire guide advancement.

There is also a need for a catheter insertion apparatus that offers the ability to visualize flash in the wire tube or the like (which also includes the ability to re-confirm flash in the wire tube or the like), and also start the wire guide inside the needle and near the needle tip, which both reduces wire reach length and reduces wire advancement dead length for improving ease and speed of catheterization.

Furthermore, there is a need for a catheter insertion apparatus that offers the ability to visualize flash in the wire advancement tube or the like (which also includes ability to re-confirm flash in wire tube or the like), and also separate the wire advancement portion of the wire tube from the blood flash chamber portion of the wire tube, which reduces the potential for blood exposure to occur during insertion and for cross-contamination between the blood from the blood flash and the external portion of the wire.

Additionally, a need exists for a catheter insertion device that allows for intuitive, easy, safe, and fast catheter placement into a patient's vasculature.

SUMMARY

The foregoing needs are met, to a great extent, by the present disclosure of a catheter insertion apparatus discussed herein. The catheter insertion apparatus comprises a needle including a needle body connected to a needle hub, the needle body having a longitudinal bore and a distal needle tip configured to pierce a wall of a blood vessel, and the needle hub having an internal flow passage in fluid communication with the longitudinal bore of the needle body; a catheter configured to removably fit over the needle body, the catheter including a catheter body connected to a catheter hub; a housing including an elongated housing body is connected to the needle hub, the elongated housing body having an elongated lumen in fluid communication with the internal flow passage of the needle hub; a guide assembly slidably mounted to the housing body and including a guidewire having a distal guidewire tip, the guidewire operable to move between a retracted position in which the distal guidewire tip is located within the needle body and an extended position in which the distal guidewire tip is located outside of the needle body; and a continuous flashback chamber is defined by the elongated lumen of the housing body and the internal flow passage of the needle hub, the continuous flashback chamber configured to allow visualization of a continuous flow of blood during insertion of the distal needle tip into the blood vessel.

According to another aspect of the disclosure, the continuous flashback chamber is operable to receive the continuous flow of blood during insertion of the distal needle tip into the blood vessel when the guidewire is in the retracted position, when the guidewire is in the extended position, and during movement of the guidewire between the retracted and extended positions.

According to another aspect of the disclosure, a flow diverter is configured to divert a flow of blood from the internal flow passage of the needle hub into the elongated lumen of the housing body.

According to another aspect of the disclosure, the flow diverter includes a through-hole configured to slidably receive the guidewire.

According to another aspect of the disclosure, the flow diverter forms a seal with a portion of a distal end of the housing body that restricts the flow of blood from leaking out of the housing.

According to another aspect of the disclosure, the guide assembly further comprises an actuator connected to a proximal end of the guidewire, the actuator being movable relative to the housing and the needle to correspondingly move the guidewire relative to the housing and the needle between the retracted and extended positions.

According to another aspect of the disclosure, the actuator includes a collar configured to slidably mount to the housing body.

According to another aspect of the disclosure, the actuator further includes a handle connected to the collar for manually sliding the collar along a longitudinal length of the housing body.

According to another aspect of the disclosure, the housing body further includes an annular band configured to abut the collar of the actuator when the guidewire is at its retracted position.

According to another aspect of the disclosure, the actuator further includes a slide member extending inwardly from the collar, the slide member having a neck portion and a head portion.

According to another aspect of the disclosure, the proximal end of the guidewire is connected to the head portion of the slide member.

According to another aspect of the disclosure, the housing body further comprises a longitudinal track configured to slidably receive the head portion of the slide member.

According to another aspect of the disclosure, the housing body further comprises a longitudinal slot configured to slidably receive the neck portion of the slide member.

According to another aspect of the disclosure, the actuator further includes an indicator configured to line up with corresponding indicia disposed along the housing body to indicate a distance of guidewire movement into the blood vessel during an insertion procedure.

According to another aspect of the disclosure, the housing body is generally tubular.

According to another aspect of the disclosure, the housing body comprises a substantially crescent shaped cross-section.

According to another aspect of the disclosure, the housing body and the needle hub comprise a transparent material or a translucent material.

According to another aspect of the disclosure, a quick flashback chamber is configured to allow visualization of an initial flow of blood upon insertion of the distal needle tip into the blood vessel.

According to another aspect of the disclosure, the quick flashback chamber is defined between the needle body and the catheter body, and wherein the needle body includes a side port to direct the initial flow of blood into the quick flashback chamber.

According to another aspect of the disclosure, a vent plug connected to a proximal end of the housing body and configured to prevent blood leakage from the lumen of the housing body.

According to another aspect of the disclosure, the needle hub further comprises a safety guard configured to provide sharps protection to the distal needle tip.

According to another aspect of the disclosure, a catheter insertion apparatus comprises a needle body having a longitudinal bore and a sharp distal needle tip configured to puncture a wall of a blood vessel; a needle hub connected to the needle body, the needle hub having an internal flow passage in fluid communication with the longitudinal bore of the needle body; a catheter configured to removably fit over the needle body, the catheter including a catheter body connected to a catheter hub; an housing including an elongated housing body connected to the needle hub, the elongated housing body having a lumen in fluid communication with the internal flow passage of the needle hub; a guidewire received within the housing body and having a distal guidewire tip, the guidewire operable to move between a retracted position in which the distal guidewire tip is located within the needle body and an extended position in which the distal guidewire tip is located outside of the needle body; a continuous flashback chamber defined by the lumen of the housing body and the internal flow passage of the needle hub, wherein the continuous flashback chamber is operable to receive a continuous flow of blood before, during, and after movement of the guidewire between its retracted and extended positions; and a safety guard removably received in the needle hub and configured to provide sharps protection for the distal needle tip.

According to another aspect of the disclosure, the elongated housing body further includes an elongated guidewire track configured to receive the guidewire.

According to another aspect of the disclosure, a flow diverter is configured to divert a flow of blood from the internal flow passage of the needle hub into the elongated lumen of the housing body, and further configured to prevent blood from leaking into the guidewire track.

According to another aspect of the disclosure, the flow diverter includes a through-hole configured to slidably receive the guidewire.

According to another aspect of the disclosure, an actuator is connected to a proximal end of the guidewire, the actuator having a slide member having a portion configured to slidably mount within the track of the housing body, the actuator operable to move the guidewire between the retracted and extended positions.

According to another aspect of the disclosure, the housing body comprises a substantially crescent shaped cross-section.

According to another aspect of the disclosure, a quick flashback chamber is defined between the needle body and the catheter body, the quick flashback chamber configured to allow visualization of an initial flow of blood upon insertion of the distal needle tip into the blood vessel.

According to another aspect of the disclosure, the safety guard comprises a safety cartridge and a safety cap that cooperate with each other to define an interior cavity, and wherein the safety cartridge and the safety cap are configured to slide over the needle body toward the distal needle tip to receive the distal needle tip within the interior cavity.

According to another aspect of the disclosure, a pivotable latch is located within the interior cavity, the pivotable latch having a distal opening and a proximal opening both sized to allow the needle body to pass therethrough.

According to another aspect of the disclosure, a biasing member is configured to cant the pivotable latch into locking engagement with the needle body to prevent removal of the distal needle tip from the interior cavity when the needle tip is within the cavity.

According to another aspect of the disclosure, the biasing member comprises a spring configured to bias the pivotable latch cant about the needle body.

There has thus been outlined certain embodiments of the disclosure in order that the detailed description thereof may be better understood, and in order that the present contribution to the art may be better appreciated. There are additional embodiments of the disclosure that will be described below and which form the subject matter of the claims appended hereto.

In this respect, before explaining at least one aspect of the catheter insertion apparatus in detail, it is to be understood that the catheter insertion apparatus is not limited in its application to the details of construction and to the arrangements of the components set forth in the following description or illustrated in the drawings. The catheter insertion apparatus is capable of aspects in addition to those described, and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the catheter insertion apparatus. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the catheter insertion apparatus are illustrated by way of examples in the accompanying drawings, in which like parts are referred to with like reference numerals throughout.

FIG. 2 is a side elevation view of the catheter insertion apparatus of FIG. 1.

FIG. 3 is a top plan view of the catheter insertion apparatus of FIG. 1.

FIG. 8A is a front perspective view of a flow diverter of the catheter insertion apparatus of the present disclosure.

FIG. 8B is a rear perspective view of the flow diverter shown in FIG. 8A.

FIG. 9 is a top plan view of a portion of the catheter insertion apparatus of the present disclosure.

FIG. 12A is an enlarged top plan view of an implementation of a distal needle tip of the present disclosure.

FIG. 12B is an enlarged top plan view of another implementation of a distal needle tip of the present disclosure.

FIG. 13A is a top perspective view of an implementation of a blood containment and vent plug of the present disclosure.

FIG. 13B is a bottom perspective view of the blood containment and vent plug of FIG. 13A.

FIG. 13C is a top perspective view of another implementation of a blood containment and vent plug of the present disclosure.

DETAILED DESCRIPTION

As will be discussed in detail herein, the present disclosure describes an integrated over-the-needle catheter insertion apparatus operable to provide continuous blood flash visibility during catheterization. The catheter insertion apparatus is operable to provide continuous blood flash visibility (i.e. flash through a catheter, flash in a wire tube, ability to re-confirm flash in the wire tube, and ability to see flash in the wire tube both during and after wire guide advancement). The catheter insertion apparatus is also operable to provide the continuous blood flash visibility while starting the wire guide tip inside and near the needle tip, without causing excessive blood exposure, and without impacting other critical aspects of an insertion procedure. The catheter insertion device of the present disclosure therefore improves insertion success rates and increases the confidence of practitioners in knowing that the needle tip is located inside the vessel throughout the entire insertion procedure without causing excessive blood exposure. The present catheter insertion apparatus may be utilized for catheterization of various vessels, including the radial artery or other arterial vessels, as well as the venous vasculature. Further, the present catheter insertion apparatus may be utilized to insert an introducer catheter used for facilitating the insertion of other catheters, such as a PICC (Peripherally Inserted Central Venous Catheter) or CVC (Central Venous Catheter) or other vascular access devices.

Figure 1:
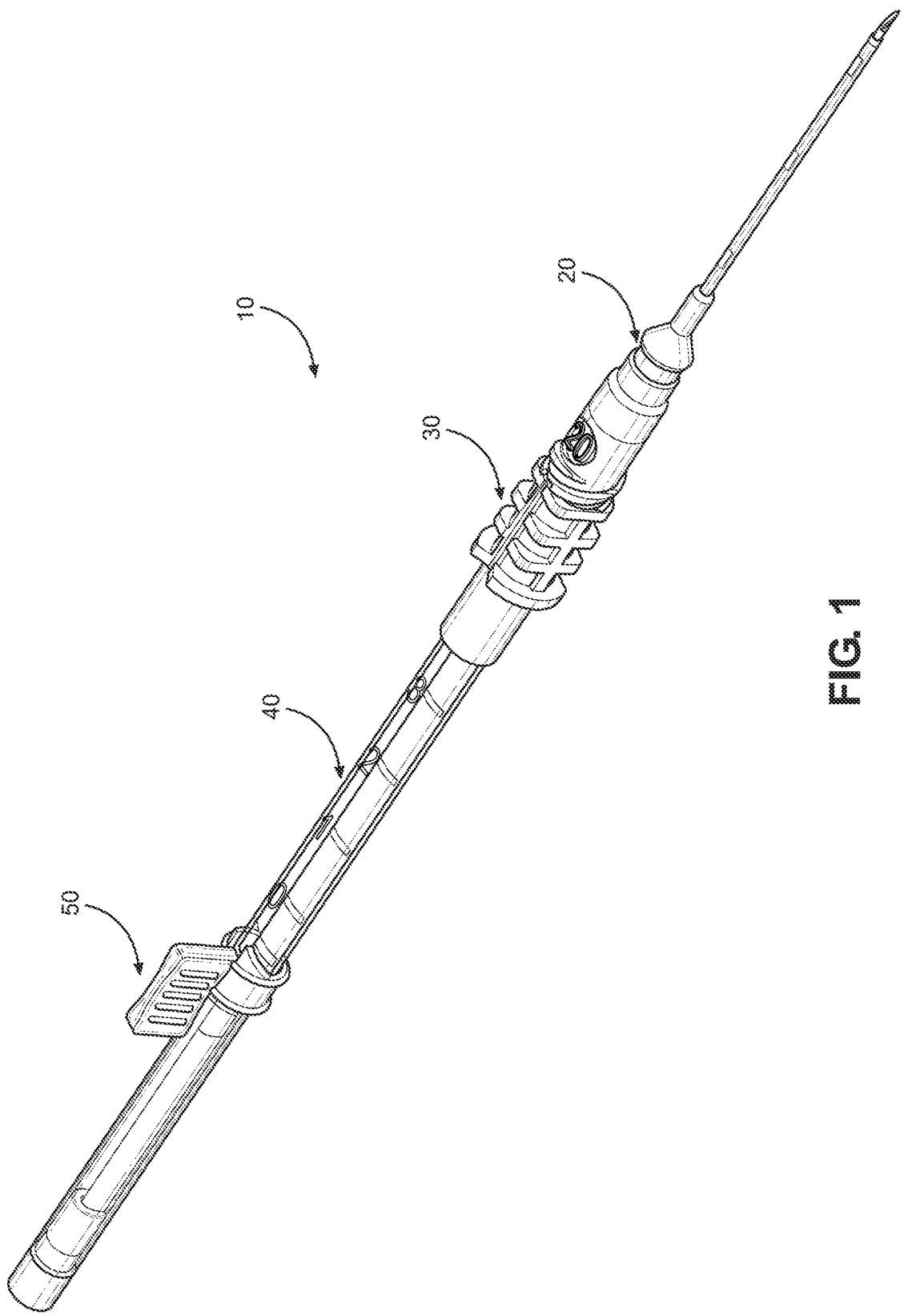
FIG. 1 is a perspective view of a catheter insertion apparatus according to an implementation of the present disclosure.

FIGS. 1-3 illustrate a catheter insertion apparatus 10 according to an implementation of the present disclosure. The catheter insertion apparatus 10 comprises an over-the-needle catheter 20, a needle 30, a housing 40, and a movable integrated guide assembly 50. The catheter insertion apparatus 10 is configured to provide continuous blood flash visibility during catheterization, including before moving the guide assembly 50, during movement of the guide assembly, and after movement of the guide assembly.

The catheter 20 includes a distal catheter end 20*a* and a proximal catheter end 20*b*. The needle 30 likewise includes a distal needle end 30*a* and a proximal needle end 30*b*. The proximal end 20*b* of the catheter 20 is configured to fit over the distal end 30*a* of the needle 30 when assembled together. The catheter 20 and the needle 30 cooperate to form a first or quick blood flashback chamber 24, as will be described in further detail below. The housing 40, or wire tube, comprises an elongated generally tubular body 42 having a distal housing end 42*a* and a proximal housing end 42*b*. The housing body 42 includes a longitudinal groove or channel that defines an elongated guidewire track 43 configured to cooperate with the guide assembly 50. The guidewire track 43 extends from the distal housing end 42*a* to the proximal housing end 42*b* of the housing body 42. The housing body 42 also includes a longitudinal lumen 44 that cooperates with a needle hub 32 of the needle 30 to define a second or continuous blood flashback chamber. The guidewire track 43 and the portion of the second flashback chamber extending from the distal end 42*a* to the proximal end 42*b* of the housing body 42 may further extend substantially parallel to one another.

The distal end 42*a* of the housing body 42 is secured to the proximal end 30*b* of the needle 30. In some instances, the needle assembly 30 may be removably connected to the housing 40. In other instances, the needle assembly 30 may be integral with the housing 40. The distal end 42*a* of the housing body 42 is connected to a flow diverter 60 configured to provide a visible continuous or uninterrupted blood flash within the second flashback chamber by directing blood into the second flashback chamber and away from the guidewire track 43. The proximal end 42*b* of the housing body 42 is sealed by a removable blood containment and vent plug 70, as will be described in further detail below. The guide assembly 50 comprises an actuator 52, such as a slider, connected to a proximal end 59*b* of a guidewire 59. The guide assembly 50 is configured to move along a longitudinal length of the housing 40 by correspondingly sliding the actuator 52.

Figures 4A, 4B, 4C, 4D:
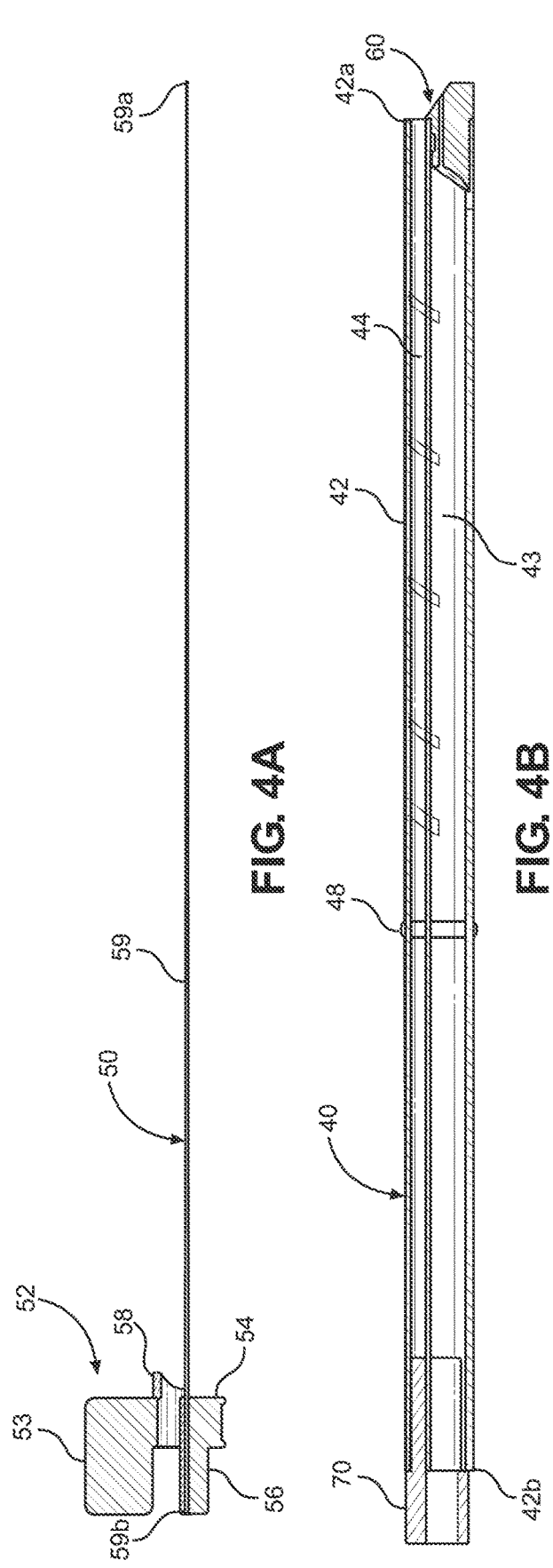
FIG. 4A is a cross-sectional side elevation view of a guide assembly of the catheter insertion apparatus of the present disclosure.
FIG. 4B is a cross-sectional side elevation view of an housing assembly of the catheter insertion apparatus of the present disclosure.
FIG. 4C is a cross-sectional side elevation view of a needle assembly of the catheter insertion apparatus of the present disclosure.
FIG. 4D is a cross-sectional side elevation view of a catheter of the catheter insertion apparatus of the present disclosure.

Referring to FIGS. 4A-4D, each of the aforementioned components of the catheter insertion apparatus 10 are separately shown prior to assembly for illustration purposes. In particular, FIG. 4A depicts the guide assembly 50 comprising the guidewire 59 and its actuator 52. FIG. 4B shows the body 42 of the housing 40 which receives the guidewire 59 and slidably carries its actuator 52. The housing body 42 is connected to the needle 30 shown in FIG. 4C, where the needle 30 includes a needle hub 32 and a hollow needle body 36. The needle 30 carries the over-the-needle catheter 20 as shown in FIG. 4D, where the catheter 20 includes a catheter hub 22 and a catheter body 26.

Figure 5A:
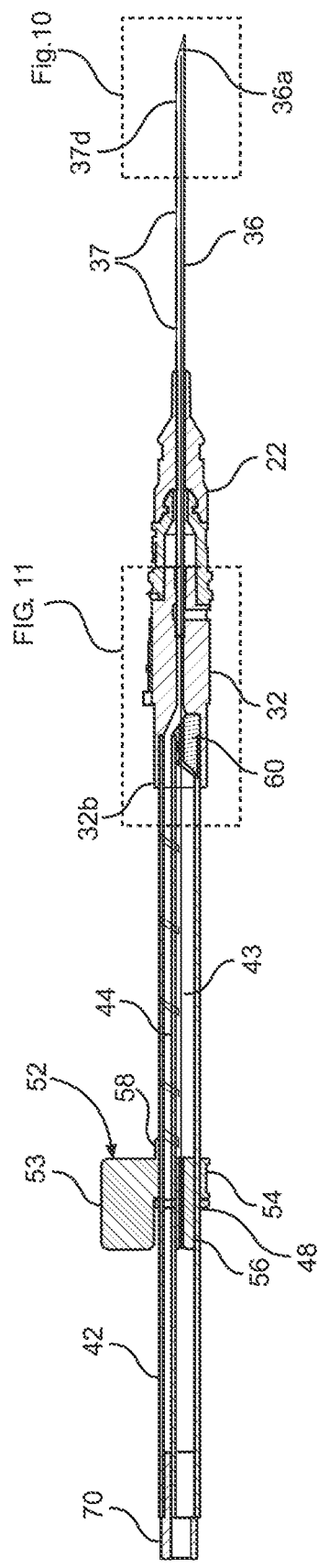
FIG. 5A is a cross-sectional side elevation view of the catheter insertion apparatus in a retracted position as taken along lines 5A-5A of FIG. 3.

In FIG. 5A, a cross-sectional view of the catheter insertion apparatus 10 is shown in its assembled state prior to use, in which the housing 40 removably carries the catheter 20 on the needle 30 in an over-the-needle position, and where the guide assembly 50 is in its normal retracted position. In this retracted position, the distal end 59*a* of the guidewire 59 is located within the needle body 36. The needle 30 is of a length in relation to the catheter 20 such that when the catheter 20 is secured on the needle 30, the distal end 30*a* of the needle assembly 30 extends beyond the distal end 20*a* of the catheter 20.

Figure 5B:
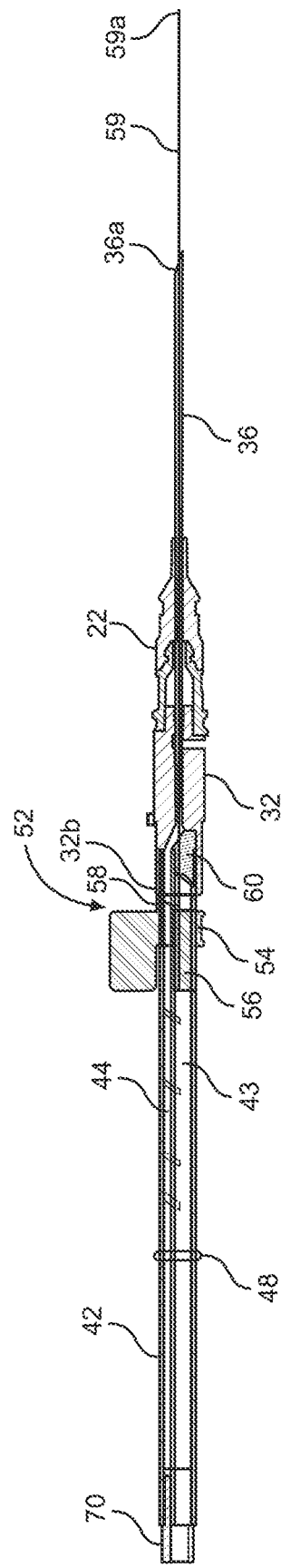
FIG. 5B is a cross-sectional side elevation view of the catheter insertion apparatus of FIG. 5A in an extended position

FIG. 5B depicts a cross-sectional view the catheter insertion apparatus 10 during a catheterization procedure in which the guide assembly 50 is in its fully extended position for guiding the insertion of the catheter body 26 into a blood vessel. The needle 30 is connected to the housing body 42, which body 42 also carries the actuator 52 of the guide assembly 50. The actuator 52 is shown moved along the length of the housing body 42 to distally advance the guidewire 59 from its normal retracted position to an extended position. The actuating handle or wing 53 is located such that it may be manipulated by a thumb of the user placing the catheter body 26 into the blood vessel while the housing 40 and/or the needle 30 is grasped to facilitate either one handed or two handed operation of the apparatus 10. Further, a flexible portion of the catheter 20 allows the catheter to be bent at large angles without kinking, i.e., after insertion in the vasculature. Also, an auxiliary device, such as a valve or tubing, may be connected to the catheter hub 22 after insertion into the vasculature.

Turning back to FIG. 4A, a distal end 59*a* of the guidewire 59 includes a rounded tip, such as a semi-spherically shaped tip, for minimizing or preventing injury to a blood vessel during insertion. The proximal end 59*b* of the guidewire 59 is securely attached to the actuator 52. The actuator 52 includes a cylindrical collar 54 configured to slide over the tubular body 42 of the housing 40. A handle or wing 53 is connected to the collar 54 for moving the actuator 52 and guidewire 59 along the length of the housing body 42. The handle 53 may be ergonomically shaped, and may further comprise an anti-slip surface, such as ridges or bumps, to provide a non-slip grip. A slide member 55 is also connected to the cylindrical collar 54 and configured to slide within the longitudinal groove 43 of the housing body 42.

Figure 7:
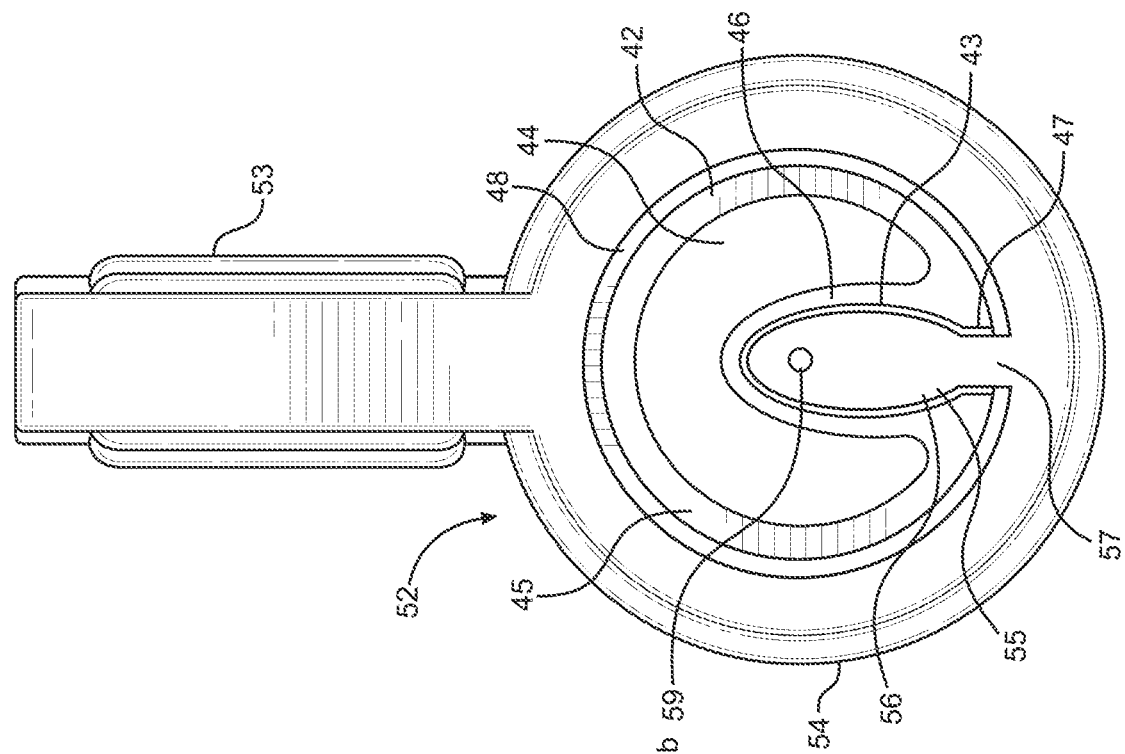
FIG. 7 is a front cross-sectional view of the actuator taken along lines 7-7 of FIG. 6.
Figure 6:
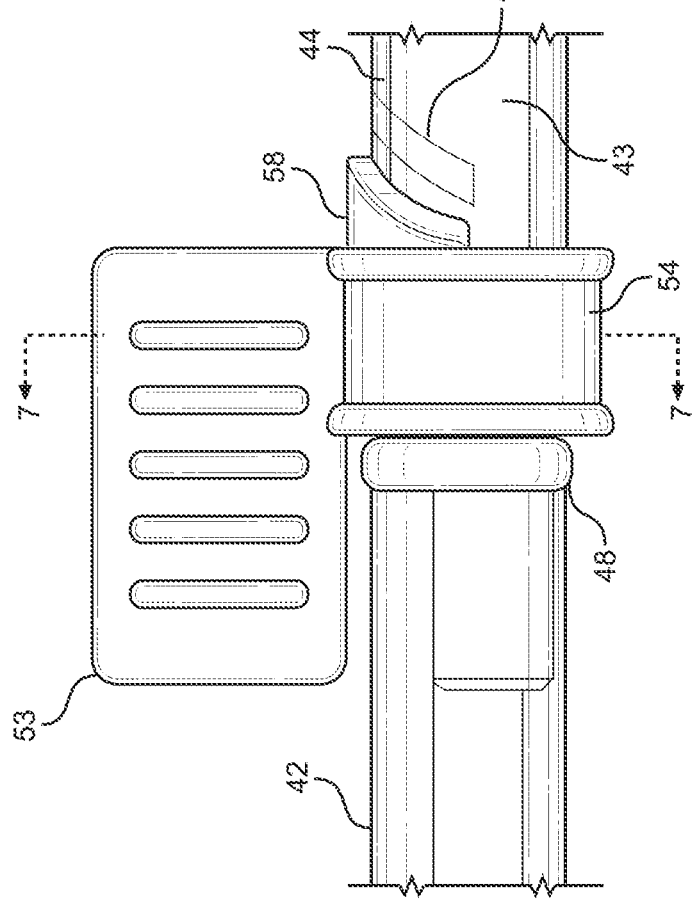
FIG. 6 is an enlarged side elevation view of an actuator of the catheter insertion apparatus of the present disclosure.

With reference to FIGS. 6 and 7, the relationship between the actuator 52 and the housing body 42 is depicted. In particular, the housing body 42 includes a generally round outer wall 45 configured to cooperate with the cylindrical collar 54, and a generally oblong inner wall or dividing wall 46 that forms the longitudinal groove 43 and is configured to slidably receive the slide member 55. The outer wall 45 and the inner wall 46 further form the longitudinally extending lumen 44 that cooperates with the needle hub 32 to define the second flashback chamber. Further, the contiguous portions of the outer and inner walls 45, 46 form a longitudinal slot 47 extending parallel to and alongside the longitudinal guidewire track 43. In some instances, the lumen 44 may comprise a substantially crescent-shaped cross-section defined by the outer and inner walls 45, 46. Both the outer wall 45 and the inner wall 46 may be transparent or translucent so that blood flash within the flashback chamber is readily visible. Centrally in the housing body 42, the inner wall or divider wall 46 is shaped to provide the longitudinally extending medial track 43 to receive a bulbous head 56 of the slide member 55. Further, a slot 47 coextensive with the track 43 and defining an opening to the track is provided in the outer wall 45 of the body 42. The slot 47 is in communication with the track 43, and is also configured to receive a neck 57 of the slide member 55 to secure the actuator to the housing body and prevent the actuator from rotating about the housing.

Turning back to FIGS. 4B and 4C the housing body 42 has a distal end 42a and a proximal end 42b. The lumen 44 and the guidewire track 43 are open through the proximal end 42b of the housing body 42. An open end of the lumen 44 at the distal end 42a of the housing body 42 cooperates with an internal flow passage of the needle hub 32 to form the continuous flashback chamber. The proximal end 42b of the lumen 44 of the housing body 42 is closed against blood flow by a porous blood containment and vent plug 70 that is configured to enable the purging of air.

As previously described, the needle 30 has a distal end 30a and a proximal end 30b, and comprises a needle hub 32 and a needle body 36. The needle hub 32 has a distal end 32a and a proximal end 32b, and the needle body 36 has a sharp beveled distal tip 36a and a proximal end 36b. The needle hub 32 may be transparent or translucent to allow visualization of blood therein. Further, the needle hub 32 includes a flow passage extending therethrough and defining a narrow portion 33 and a countersink portion 34. An internal cavity 35 is provided at the proximal end 32b of the needle hub and is configured to receive a portion of the distal end 42a of the housing body 42. The countersink portion 34 of the flow passage is disposed between the fluid narrow portion 33 and the internal cavity 35.

The needle body 36 has an internal needle lumen or bore 36c extending from its distal tip 36a to its proximal end 36b. The needle body includes at least one side port or flashback blood port 37 configured to allow a flow of blood into the quick blood flashback chamber 24. The proximal end 36b of the needle body 36 is fixedly secured to the distal end 32a of the needle hub 32 so that the internal needle bore 36c is in fluid communication with the internal flow passage, including the narrow and countersink portions 33, 34. Further, the internal flow passage of the needle hub cooperate with the lumen 44 of the housing body 42 to define the continuous blood flashback chamber. The needle hub 32 may further include a grip member 39, such as a protruding rib, to assist a user in gripping the needle assembly 30 during an insertion procedure.

FIG. 4D shows the catheter 20, which has a distal end 20a and a proximal end 20b. The catheter assembly 20 also includes a catheter hub 22 and a catheter body 26, the catheter body 26 having a distal tip 26a and a proximal end 26b. The catheter body 26 further includes an internal lumen or bore 26c extending from the distal tip 26a to the proximal end 26b. When the catheter insertion apparatus 10 is assembled, the distal end 42a of the housing body 42 is securely received within the proximal end 32b of the needle hub 32, and the catheter 20 is fit over the needle body 36 of the needle assembly 30. The elongated lumen 44 of the of the housing 40 is in fluid communication with the needle bore 36c via fluid communication with the internal flow passage of the needle hub 32. The distal tip 26a of the catheter body 26 may include a progressively decreasing cross-section or taper to facilitate insertion into the blood vessel. Further, the catheter body 26 is supported at its proximal end 26b by the catheter hub 22 which may comprise laterally projecting suture wings (not shown) in some implementations, although it should be understood that the catheter hub 22 may be provided with other means for retention of the catheter assembly 20 on the patient after placement in the blood vessel.

Disposed within the distal end 42a of the housing body 42 and within the proximal end 32b of the needle hub 32 closing off the distal end 42a of the guidewire track 43 is a flow diverter 60 having a distal end 60a and a proximal end 60b. As shown in FIGS. 8A and 8B, the distal end 60a of the flow diverter includes a slanted surface 62 configured to divert a flow of fluid from the internal passage of the needle into the lumen 44 of the housing 40. The flow diverter 60 further comprises a passage or through-hole 64 configured to allow the guidewire 59 to slidably pass therethrough without interrupting fluid communication between the needle bore 36c and the lumen 44. As a result, a blood flashback into the second flashback chamber is continuous irrespective of the movement of the guidewire along the length of the housing and the needle.

In particular, the passage 64 is formed by a guidewire receiving opening extending from distal end 60a to the proximal end 60b, and through which the guidewire 59 is passed for longitudinal movement relative to the housing 40. The fit between the guidewire 59, which may have a uniform diameter, and the passage 64 is such as not to interfere with easy sliding movement of the guidewire 59, and at the same time, to prevent or minimize a flow of blood therethrough and into the guidewire track 43. This is accomplished because the proximal end 60b of the flow diverter 60 is configured to snugly fit within the guidewire track 43 at the distal end 42a of the housing body 42, and thus the track 43 is closed at the distal end 42a of the housing body 42.

The guidewire track 43 remains open at the proximal end 42b of the body 42 and along its bottom surface via the coextensive slot 47 longitudinally extending and medially disposed in the outer wall 45 of the housing body 42. The distal surface or end 60a of the diverter 60 therefore diverts the flow of flashback blood into the adjoining lumen portion 44 of the continuous flashback chamber at the distal end 42a of the housing body 42. The flow diverter restricts a flow of blood from entering the guidewire track 43, such that any blood leakage through the diverter passage 64 and into the guidewire track 43 would be minimal. Furthermore, other configurations of the diverter may include a silicon seal that creates a tight seal around the wire, and a duck-bill seal that accomplishes a similar liquid tight seal.

In some implementations, the continuous flashback chamber may be used for a catheter insertion procedure into the venous system as well as into the arterial system. The venous system has a lower pressure which causes a slower flow rate. Additionally, there is no observable pulsatile blood return in the venous system as is in the artery. This provides an increased difficulty in observing blood flowing as it's much harder to see a slow blood return from the quick pulsatile blood return. To compensate for this, the continuous flashback chamber may have a smaller cross-sectional area so that the flow of blood can still be observed. In some aspects, the continuous flashback chamber may be helical or spiral shaped, or other significantly curved shape, to compensate for a smaller volume of blood flow therein.

In another implementation, the continuous flashback chamber may comprise a plurality of vertical cavities disposed within the interior of the chamber. For instance, each cavity may be spaced apart approximately every 2 mm. When the blood flow reaches a vertical cavity, it wicks upward and fills the empty space which is easily observable to the practitioner. The practitioner is therefore able to observe blood continuously wicking upward into the subsequent vertical cavities within the lumen. In another implementation, several separate pieces of a gauze or paper-like material may be disposed within the vertical cavities in order to quickly soak up blood along the length of the flash chamber to further improve the wicking ability.

Referring again to FIG. 4C, the needle 30 includes an elongated needle body 36 of a gauge generally in the range of 16-24. The needle body 36 is mounted at its proximal end 36b on the needle hub 32 and has a beveled distal tip 36a. The needle hub 32 has a proximal end 32b and a distal end 32a. The distal end 32a of the needle hub 32 comprises a male luer connector, such as a male luer slip tip 38, configured and sized for a fluid tight, yet releasable, connection to a corresponding female luer connector 28 provided at the proximal end 20b of the catheter hub 22. The proximal end 32b of the needle hub 32 is sized and configured to receive a portion of the distal end 42a of the housing body 42.

The needle body 36 includes a needle bore 36c of uniform cross-section which receives the guidewire 59 with suitable clearance, and the beveled distal tip 36a of the needle body 36 is orientated upward. A flashback blood port 37 is provided on an uppermost surface of the needle body 36. In some instances, a plurality of blood ports 37 may be provided along the uppermost surface of the needle body 36. For instance, the ports 37 may be arranged in spaced relation with each other along a length of the needle body 36. The blood ports 37 provide an opening for the entrance of blood into the quick flashback chamber 24. More specifically, the ports 37 in the needle body 36 are spaced proximally of the beveled distal tip 36a to provide an intermediate section of the elongated needle body 36 which is configured to cooperate with the elongated catheter body 26 to define the quick flashback chamber 24 located between the outside wall of the needle body 36 and the inside wall of the catheter body 26.

During catheterization, the guidewire actuator 52 is used for moving the guidewire 59 within the guidewire track 43 of the housing body 42 through a stroke spanning a length of the track. Such movement of the actuator 52 distally along the housing body 42 toward the needle 30, as shown in FIG. 5B, results in the rounded or spherical distal tip 59a of the guidewire 59 projecting beyond the distal tip 36a of the needle assembly 30 and into the blood vessel so that the guidewire 59 can guide the catheter into a desired placement within the blood vessel. The guidewire actuator 52 includes an upstanding actuating handle or wing 53 which projects away from the housing body 42 and is in a readily accessible position for the user. The cylindrical collar 54 of the actuator is operable to slide along the outer wall 45 of the housing body 42. The slide member 55 projects inwardly from the collar 54.

As previously mentioned, the slide member 55 includes the bulbous head 56 and the neck 57 which slidably fit in the guidewire track 43 and the slot 47, respectively. The head 56 and the neck 57 of the actuator 52 are thus operable to prevent rotation of the actuator about the housing body 42. Further, the bulbous head 56 is attached to the proximal end 59b of the guidewire 59 for advancing and retracting the guidewire in response to movement of the actuator 52 between its limit positions.

The actuator 52 may also include an indicator 58 connected to the collar 54 and configured to line up with indicia 49 disposed along the length of the housing body 42 in order to indicate a distance that the guidewire 59 has moved relative to housing body 42 and into the blood vessel during an insertion procedure. As shown in FIG. 9, the indicator 58 and indicia 49 may be correspondingly shaped. For instance, the indicator 58 and indicia 49 may have a chevron shape. The indicia 49 may further include spaced apart alphanumeric markings 49a to indicate a specific distance of guidewire advancement along the housing body 42. For instance, such markings may be spaced every centimeter from a home position 49b (i.e., to allow for 3.5 cm of guidewire advancement along a 4 cm catheter).

Further, the home position 49b may have an arrow shaped marking to help confirm that the guidewire is not advanced during vessel puncture. The distal tip 59a of the guidewire 59 is positioned at the heel of the needle bevel when the indicator 58 reaches a first mark (i.e., a "0" mark) during guidewire advancement. Further, the housing body 42 may include an annular band 48 having a larger diameter than the outer diameter of the body 42 to act as a bump against which the collar 54 of the actuator 52 is configured to abut and pass over when the guide assembly 50 is proximally retracted from a distally extended position. For instance, the resistance created between the annular band 48 and the collar 54 makes it difficult, but possible, for a user to retract the actuator 52 past the annular band 48.

Referring again to FIG. 5A, at the start of a catheterization procedure, the actuator 52 is disposed in the fully retracted position. In this fully retracted position, the rounded distal tip 59a of the guidewire 59 may be located proximal of the distal tip 36a of the needle assembly 30 and in a clearance position with respect to the most distal needle port 37d so as not to inhibit an early visualization of blood flashback into a space between the needle body 36 and the catheter body 26. Upon movement of the actuator 52 from its initial retracted position toward its fully extended position, i.e., toward the distal end 42a of the housing body 42 as shown in FIG. 5B, the indicator 58 will contact and abut the proximal end 32b of the needle hub 32. Such contact limits further movement of the actuator 52 as well as the corresponding amount of extension of the distal tip 59a of the guidewire 59 past the distal tip 36a of the needle and into the blood vessel.

Figure 10:
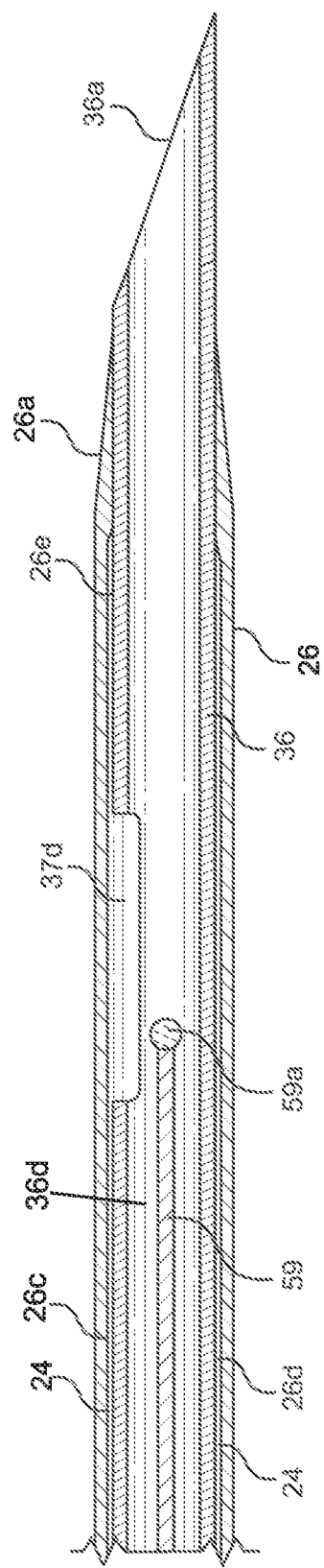
FIG. 10 is an enlarged cross-sectional side elevation view of the portion of the catheter insertion apparatus demarcated in FIG. 5A showing a distal end of the catheter insertion apparatus of the present disclosure.

An annular space formed between the needle body 36 and the catheter body 26 defines the quick blood flashback chamber 24. Stated another way, the quick blood flashback chamber 24 has an annular cross-section and is disposed between the catheter body 26 and the needle body 36 when catheter assembly 20 is carried on the needle assembly 30 in the over-the-needle position. With particular reference to FIG. 10, the internal bore 26c of the catheter body 26 forms a relatively shallow longitudinally extending well or recess 26d with the needle body 36, where the distal portion 26e of the well 26d is located distally of the distal-most flashback port 37d, and where the proximal end of the well is located proximally of the proximal-most flashback port provided in the uppermost surface of the needle body 36.

The interior wall of the catheter body 26 and the exterior wall of the needle body 36 form a snug fit that may be fluid tight between the distal portion 26e of the well 26d and the distal end or tip 26a of the catheter body 26. Thus, no fluid leakage will occur between the distal end of the quick flashback chamber 24 and the tip 36a of the needle body 36 when blood flows from a vessel through the needle bore 36c and into the first flashback chamber 24 through ports 37. The catheter hub 22 and the needle hub 32 similarly form a snug fit at the proximal end of the annular quick flashback chamber 24 to prevent any leakage of blood. It should be appreciated that air may escape into the atmosphere through the proximal end of the annular quick flashback chamber 24 and between the male luer slip tip 38 of the needle assembly 30 and the corresponding female luer connector 28 of the catheter 20 in order to permit blood flow into the quick flashback chamber.

Further, in some instances, the spacing of the distal-most port 37d from the distal needle tip 36a may be such that only a relatively short path for blood flow exists from the beveled distal tip 36a of the needle body 36 through the needle bore 36c and into the distal-most flashback port 37d. Moreover, as shown in FIG. 10, when the guidewire 59 is in the retracted position, its spherical distal tip 59a may be disposed in a non-obstructing or clearance position in relation to the most distal or first blood flashback port 37d encountered by the initial blood flow into the needle bore 36c. In particular, the distal tip 59a of the guidewire 59 is shown substantially intermediate the distal and proximal ends of the first flashback port 37d, which provides an unobstructed flow path to the first flashback port 37d, and thus the guidewire does not interfere with entry of blood into the first flashback chamber 24. In some aspects, the rounded distal tip 59a may divert a flow of blood into the port 37d. It should be appreciated that other non-obstructing positions may be established for the guidewire 59 in relation to the first flashback port 37d.

Visualization of the blood flash will occur throughout the length of the first flashback chamber 24 due to the at least one flashback port 37 provided on the needle body 36. Moreover, the diameter of the guidewire 59 may be selected in relation to the diameter of the needle bore 36c to provide an annular blood flow passage 36d therebetween which communicates with the first flashback chamber 24 through the spaced ports 37. Thus, when the guidewire 59 is in the retracted position as shown in FIG. 10, two flow paths are established for flashback blood. Specifically, a first flow path through the multiple flashback ports 37 and into the first flashback chamber 24, and a second flow path via the annular blood flow passage 36d extending along the longitudinal extent of the guidewire 59 from its distal tip 59a, into the second flashback chamber defined by the internal flow passage of the needle hub 32 and the lumen 44 of the housing body 42.

Figure 11:
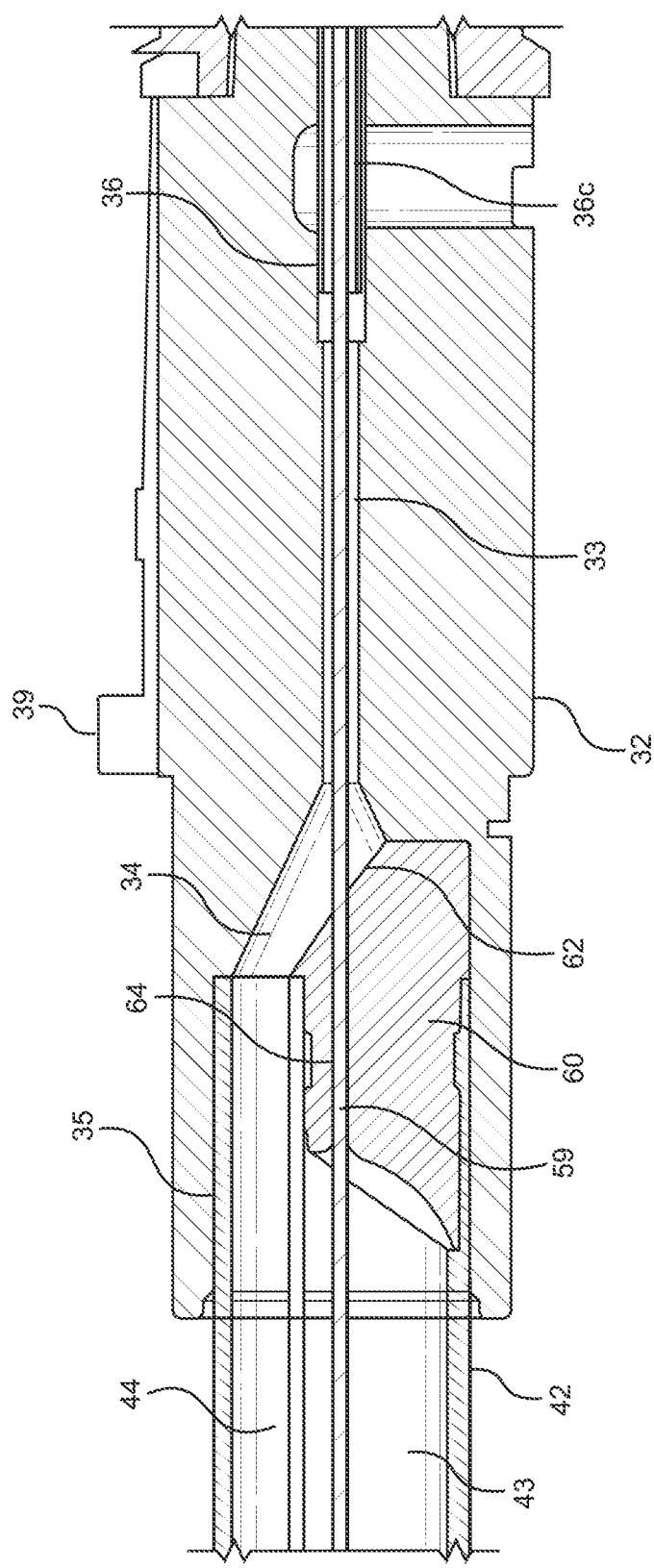
FIG. 11 is an enlarged cross-sectional side elevation view of the portion of the catheter insertion apparatus demarcated in FIG. 5A showing the proximal end of the needle assembly and the distal end of the housing.

Thus, blood flash is permitted because the outer diameter of the guidewire is small enough to allow enough flash back between the outer diameter of the guidewire and the inner diameter of the needle. In other implementations, the blood flash may be permitted due to other design features, including cutting grooves and/or slots formed into the inner surface of the needle that allow for an increased volume of blood to flow between the inner diameter of the needle and the outer diameter of the guidewire. Similarly, cutting grooves and/or slots may be formed on the outer diameter of the guidewire to allow for an increased volume of blood to flow through the space between the inner diameter of the needle and the outer diameter of the guidewire. Further, the cross sectional area of the guidewire may be varied with different patterns that add volume when the blood passes. Such varying patterns may be configured to maintain the desired rigidity necessary for guidewire wire advancement over the needle. For example, if the wire is flat pressed it has more rigidity in the vertical direction Referring now to FIG. 11, the needle hub 32 includes an internal flow passage having a narrow portion 33 which, at its distal end, communicates with the needle bore 36c and, at its proximal end, communicates with the countersink portion 34 of the internal flow passage. The countersink portion 34 in turn communicates with the lumen 44 of the housing body 42 which has a distal end 42a provided within an internal cavity 35 formed at the proximal end 32b of the needle hub 32. The internal flow passage of the needle hub 32 cooperates with the longitudinal lumen 44 of the housing body 42 to define the continuous blood flashback chamber. More particularly, blood flow from the needle bore 36c through the narrow portion 33 and the countersink portion 34 of the internal flow passage is diverted into the distal end 42a of the longitudinal lumen 44 of the housing body 42 via the slanted surface 62 of the flow diverter 60. The throughhole 64 of the diverter is configured to permit longitudinal movement of the guidewire 59 without blocking or interrupting the blood flow path into the lumen 44, and thus providing the visible continuous flow of blood during an insertion procedure.

Thus, when the hub 32 of the needle assembly 30 is mounted on the distal end of the housing body 42 and fixedly attached thereto, for example, by use of an appropriate adhesive or the like, a continuous path for flashback blood is established from the beveled tip 36a of the needle body 36 through an internal flow passage of the needle hub 32 and into the lumen 44 of the housing via the slanted surface 62 of the flow diverter 60. The needle hub 32 may also include a grip member 39 between the distal and proximal ends 32a, 32b of the needle hub. The grip member 39 is configured to assist a user in grasping the needle assembly during the catheterization procedure. The grip member 39 may include radially extending ribs circumferentially spaced apart at their outermost edges to assist the user with gripping the needle hub.

As previously described, both the needle hub 32 and the housing body 42 may be transparent or translucent to allow visualization of the continuous blood flash within the second blood flashback chamber. For instance, the needle hub 32 may be formed from a moldable thermoplastic material. The housing body 42 may be formed of a transparent or translucent, semi-rigid plastic material having some flexibility with sufficient resilience so that it maintains its generally tubular configuration during use. The needle body 36 may be formed of an appropriate metal, such as stainless steel. The blood ports 37 provided for visualization of flashback blood into the first flashback chamber 24 may be ground into the upper surface of the needle body 36. The guidewire 59 may be a spring wire fabricated of metal, such as stainless steel or nitinol. The elongated catheter body 26 may similarly be clear or translucent to provide for visualization of blood flash in the first flashback chamber 24. For instance, the catheter body 26 may be manufactured from a single lumen catheter blank of transparent or translucent polyurethane. In some implementations, the catheter insertion apparatus may further comprise a protective cover configured to fit over the catheter body 26 when the catheter 20 is fit over the needle body 36 of the needle assembly 30.

Thus, during a catheterization procedure, the user first punctures the blood vessel with the needle tip 36a of the catheter insertion apparatus 10, in which the guide assembly 50 is in its retracted position, by using a continuous and controlled forward movement so as to avoid transfixing the vessel walls. The user will know whether a successful entry of the needle tip 36*a* into the blood vessel was achieved when an immediate appearance of flash blood into the first or quick flashback chamber 24 is visible, which is followed by visualization of blood flash within the second or continuous flashback chamber.

Once the user has confirmed the desired position of the needle tip 36*a* into the blood vessel, the needle assembly 30 is stabilized and distal advancement of the guidewire 59 via the actuator 52 is carefully performed by moving through a relatively short forward stroke. As the guidewire 59 is distally advanced, the second flashback chamber receives a continuous flow of blood which lets the user know that the desired needle placement is maintained. If the user retracts the guidewire 59 while the needle tip is still in the blood vessel due to resistance encountered while advancing the guidewire, the second flashback chamber will nevertheless still receive a continuous flow of blood as long as placement of the needle tip is maintained within the blood vessel.

Once the guidewire 59 is located within the blood vessel for a length predetermined by the performed stroke of the actuator 52, the user grips the catheter hub 22 and advances the catheter 20 distally relative to the needle assembly 30. The distal end 20*a* of the catheter 20 is configured to track the position of the guidewire 59 into the blood vessel. Thereafter, while holding the catheter 20 in place within the vessel, the user may remove the needle assembly 30 from the vessel. An auxiliary device, such as an injection cap, a valve, or a medical tubing may then be attached to the luer connector 28 of the catheter hub 22.

The distal needle tip 36*a* may further comprise one or more echogenic features, in addition to the sharp tip, as depicted in FIGS. 12A and 12B. Such echogenic features may include, for example, a divot 36*e* as shown in FIG. 12A. Such a divot 36*e* is operable to improve the echogenicity of the needle tip 36*a* when observed under ultrasound. Similarly, such echogenic features may also include, for example, a through-hole 36*f* as shown in FIG. 12B. Such a through-hole 36*f* is also operable to improve the echogenicity of the needle tip 36*a* when observed under ultrasound. The visible echogenic features enable a practitioner to better visualize the location of the needle body 36 when using ultrasound imaging equipment.

As previously described, the lumen 44 and the guidewire track 43 are open through the proximal end 42*b* of the housing body 42. This open proximal end 42*b* of the lumen 44 of the housing body 42 is sealed by the porous blood containment and vent plug 70 that is configured to enable the purging of air from within the lumen while also preventing blood flow from leaking out of the proximal end 42*b* of the lumen 44. Further, the plug 70 is configured to not seal the proximal end of the guidewire track 43.

In particular, as shown in FIGS. 13A and 13B, an implementation of the plug 70 includes a plug body 72 configured to fit within the lumen 44 at the proximal end 42*b* of the housing body 42. The plug 70 further includes an enlarged plug head configured to abut the proximal end 42*b* of the housing body when the plug body 72 is inserted into the lumen 44. A longitudinal channel 75 extends through the length of the plug 70 and is configured to ensure that the guidewire track 43 is not plugged when the plug body 72 is inserted into the lumen 44. The plug body 72 and the plug head 74 therefore both may have a substantially crescent shaped cross-section corresponding to the substantially crescent shaped cross-section of the lumen 44. In another implementation, the plug 70 may further include at least one longitudinal and cylindrical vent extending through the length of the plug and operable allow the purging of air from within the lumen while also preventing blood flow from leaking out of the proximal end 42*b* of the lumen 44.

FIG. 13C illustrates another implementation of the plug 70*a* including at least one ventilation through hole 76 configured to be in direct communication with the lumen of the housing body. In other implementations, the plug may include a crescent shaped hole configured to mate with the crescent shape of the lumen of the housing, and an extruded or raised surface configured to mate with the guidewire track. Other implementations may include a bloodless plug formed integrally with the housing body. Yet other implementations may comprise a bloodless plug including a small silicon sheet that is pre-slit so that the guidewire is operable to be pushed through the slit, wherein the slit is operable to seal around the outer diameter of the guidewire. In yet other implementations, a duck-bill shaped silicon seal may be operable to allow the guidewire to be pushed therethrough, but when pressure from vasculature is exerted on the outside of the seal, it closes itself over the guidewire thus preventing blood leakage.

Other implementations may include a second chamber configured to contain blood droplets that may escape through the small clearance between the plug hole and the outer diameter of the guidewire. This blood containment area may be an empty space that allows for blood collection. The blood containment area may alternatively contain gauze or other absorbent material that further keeps blood that escaped from dripping out of the chamber. Other implementations may include a wire advancer operable to mate with the bloodless plug so that when the wire advancer is fully advanced, the bloodless plug hole is further blocked to prevent blood seepage.

Figure 14:
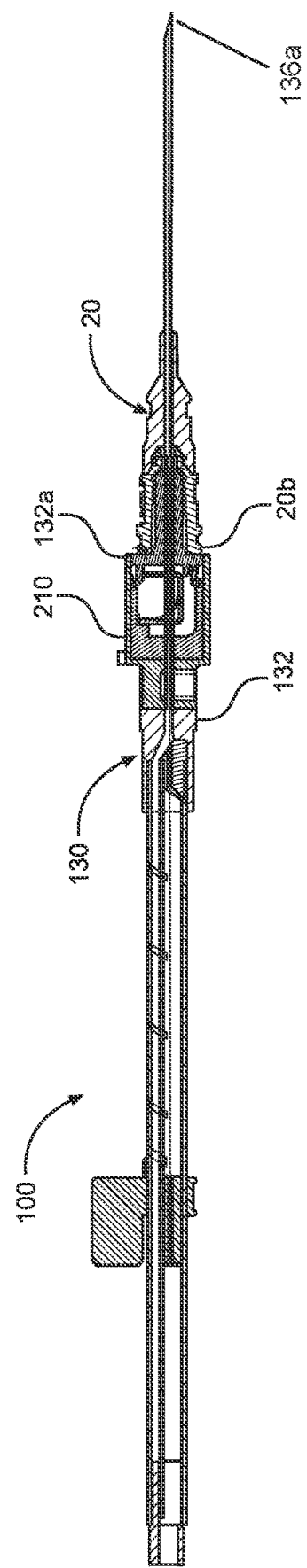
FIG. 14 is a cross-sectional side elevation view of a catheter insertion apparatus having a needle guard according to another implementation of the present disclosure.

FIG. 14 illustrates a catheter insertion apparatus 100 configured to provide continuous blood flash visibility during catheterization according to another implementation of the present disclosure. The catheter insertion apparatus 100 is similar to the catheter insertion apparatus 10 previously described above, except the catheter insertion apparatus 100 comprises a needle assembly 130 operable to provide sharps protection for the distal needle tip 136*a*. More particularly, the needle assembly 130 comprises a needle hub 132 configured to removably receive a safety guard 210 operable to provide sharps protection for the distal needle tip 136*a*.

Figure 15A:
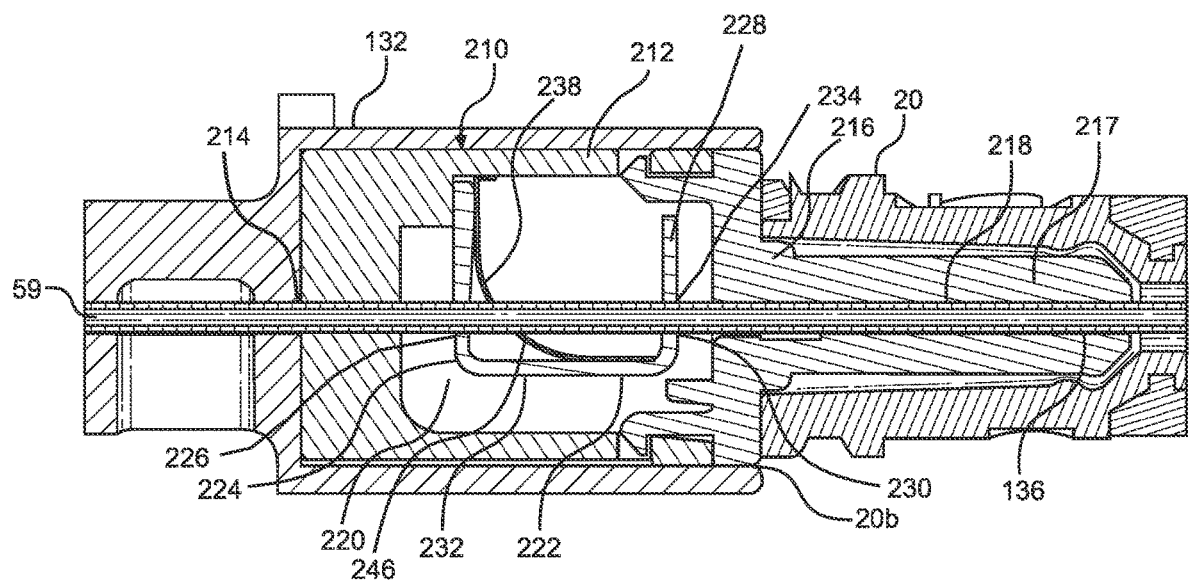
FIG. 15A is an enlarged cross-sectional side elevation view of the needle guard of FIG. 14 in an unlocked position.

FIG. 15A shows the safety guard 210 is removably provided within the distal end 132*a* of the needle hub 132. The safety guard 210 includes a generally hollow safety cartridge 212 that is formed with a proximal opening 214 at a proximal end thereof. The safety guard 210 further includes a safety cap 216 having a through hole 218 configured to slidably receive the needle body 136. The safety cap is 216 configured to releasably secure to the catheter 20. In particular, the safety cap 216 includes a tip 217 at its distal end having a pair of clips that are configured to expand when the needle is passed through the tip 217. When the clips are expanded, they mate with a corresponding inner ring disposed on an interior surface of the catheter hub for preventing the safety assembly from being easily removed from the catheter.

The safety cartridge 212 and the safety cap 216 are preferably molded from a plastic material. The safety cap 216 may be secured to the safety cartridge 212 by tab members extending from the cap and configured to securely snap into respective detents formed in the cartridge. In other implementations, the safety cap may be secured to the safety cartridge with a glue, a solvent, or some other adhesive.

Once secured together, the cartridge 212 and the cap 216 cooperate to define an interior cavity 220.

A generally U-shaped pivotable latch 222 is located within the interior cavity 220. The pivotable latch 222 has a proximal wall 224 that may define a beveled proximal opening 226, and a distal wall 228 that defines a distal opening 230. The proximal and distal walls 224 and 228 are located at opposite sides of a latch body 232. The pivotable latch 222 may be made from stainless steel or spring steel, among others. In other implementations, the pivotable latch may be molded as one piece from a plastic material. The proximal opening 226 and the distal opening 230 of the pivotable latch 222 are sized to allow the needle body 136 to pass through the openings 226 and 230. In some aspects, the proximal and distal openings 226 and 230 may be circular, coaxial, and only slightly larger than the diameter of the needle body 136 so as to permit the needle body 136 to move through the openings 226 and 230.

The distal wall 228 of the latch 222 further defines a slot 234 that communicates with the distal opening 230. The slot 234 has a width that is smaller than the diameter of the distal opening 230 and the diameter of the needle body 136. The width of the slot 234 is large enough to permit the guidewire 59 to pass therethrough. The slot 234 preferably extends from the circumference of the distal opening 230 to an upper edge of the distal wall 228. In use, the slot 234 allows the needle to pivot down while preventing the needle from pushing through the slot. Moreover, the inner cavity of the safety cartridge may include nubs that force the safety clip to tightly secure to the needle if the cartridge is forced off the needle. Further, a binding action of the proximal end of the safety clip's inner diameter may occur on the needle to lock the needle tip in place within the safety cartridge.

FIG. 15A depicts the pivotable latch 222 in a first, or unlocked, position. A biasing member 238, such as a flat spring, is provided within the interior cavity 220 and is operable to bias the pivotable latch toward a second, or locked, position shown in FIG. 15B, as will be further discussed below. The biasing member 238 is bent from its normally straight position toward a curved position such that the curved spring is compressed when loaded into the cartridge. As a result, the spring is therefore urged to un-compress in order to force the latch 222 downward when the needle bevel passes through the distal clip hole or opening 230 and into the slot.

A first end portion of the spring 238 is in contact with an upper wall of the interior cavity 220. A second end portion of the spring 238 is in contact with the body 232 of the latch 222. In particular, the second end portion of the spring 238 is welded to the body of the latch. The biasing member 238 may have a substantially rectangular center portion defining an elongated opening 246 that is generally aligned with the proximal opening 226 of the latch to allow the needle body 136 to pass through both openings 226 and 246. The opening 246 in the latch may have a diameter that is only slightly larger than the diameter of the needle body 136. The biasing member 238 may be formed from a resilient material that is operable pivot the latch to bite into the needle body 136 when in the locked position. Stated another way, the latch locks into the needle when the spring forces the clip to pivot. In some aspects, the biasing member 238 may be formed from stainless spring steel.

Turning back to the unlocked position shown in FIG. 15A, in operation the needle body 136 is inserted into the safety cartridge 212 through its proximal opening 214 and extends through the interior cavity 220, the proximal and distal openings 226 and 230 of the pivotable latch 222, and the through hole 218 of the safety cap 216, so that the needle tip 136a is located outside of the safety guard 210 during catheterization.

When the catheter is advanced forward during an insertion procedure, it pulls the safety guard with the catheter towards the needle tip. For instance, with reference to the locked position shown in FIG. 15B, when the safety guard 210 is removed from the needle hub 132 and moved toward the distal needle tip 136a, the distal needle side port or blood flashback port 137d is blocked by the safety cartridge 212 and the needle body 136 is corresponding withdrawn into the safety cartridge 212 and, further, from the distal opening 230 of the pivotable latch 222 so that the biasing member 238 moves toward a non-bent position or an uncompressed position, thereby urging the pivotable latch 222 to cant about the needle body 136. Thus, at first the safety is advanced forward due to the catheter advancement and the needle remains stationary. Then, after the catheter is fully or at least partially advanced forward, the catheter becomes stationary and the needle is pulled backwards out of the patient.

Since the pivotable latch 222 is formed from a sufficiently hard metal material, such as stainless steel, and the diameter of the proximal opening of the pivotable latch 222 is only slightly larger than the diameter of the needle body 136, the pivotable latch 222 bites into the needle body 136 to bind or lock the needle body 136 so as to prevent its further forward or rearward movement when the pivoting member or latch 222 is canted about the needle body 136 after the needle tip 136a is withdrawn into the interior cavity 220 from the distal opening 230 of the latch 222. The biasing member 238 thus provides a means for canting the pivotable latch about the needle when the needle tip is within the cavity. The canting means further engages the needle body to prevent the removal of the needle body from the safety guard. For instance, the needle tip is operable fall into the slot on the distal side of the latch to prevent forward movement of the needle, and thus lock the needle in place. The binding of the latch on the needle body prevents rearward movement. Moreover, inner nubs of the safety cartridge further encourage pivoting of the clip and improved binding of the clip on the needle for further preventing rearward movement.

Additional force applied to the needle when in the locked position results in even more binding force being applied on the needle body 136. For example, an attempt to withdraw the needle body 136 from the safety guard 210 when in the locked position causes the surface of the pivotable latch 222 to contact a surface of the interior cavity 220. This contact acts as a stop to reinforce the canting of the pivotable latch 222, and also causes the pivotable latch 222 to further bite into the needle body 136, which increasingly binds or locks the needle tip within the safety guard to prevent its further movement. Therefore, once the pivotable latch 222 has become canted about the needle body 136, further rearward movement of the needle is prevented.

Similarly, further forward movement of the needle is also prevented once the pivotable latch 222 has become canted about the needle body 136. The biasing member 238 maintains the pivotable latch 222 in its canted position with respect to the needle body 136. As a result, there can be no relative movement between the needle tip 136a and the pivotable latch 222 once the latch becomes canted about the needle body 136. Therefore, once the distal wall 228 of the pivoting latch 222 is pushed against the safety cap 216, neither the pivoting latch 222 nor the needle 202 can move further. Moreover, even if the binding force of the pivoting latch 222 on the needle body 136 could be overcome, forward movement of the needle is blocked by the slot 234 of the latch which is slightly smaller than the needle body outside diameter.

Figure 15B:
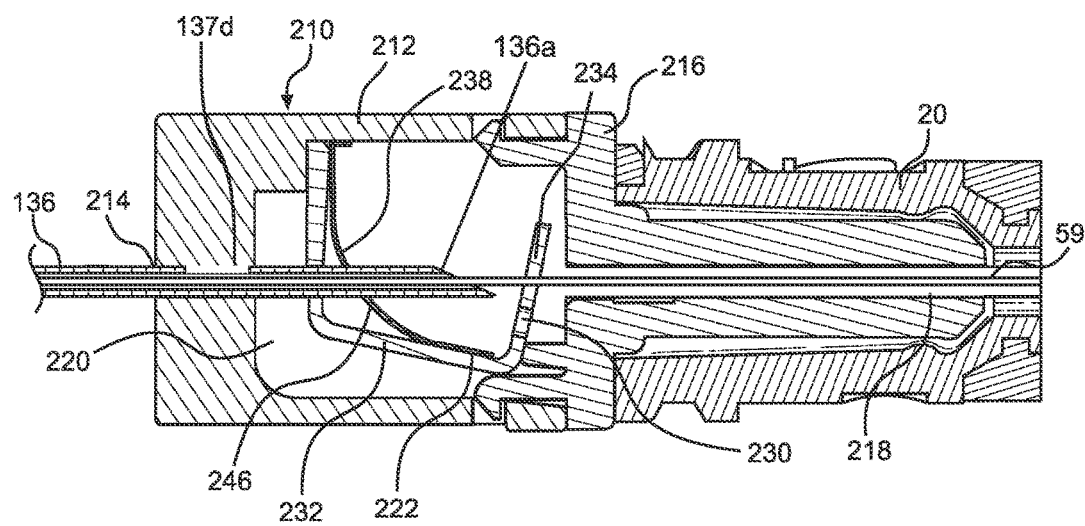
FIG. 15B is an enlarged cross-sectional side elevation view of the needle guard of FIG. 14 in a locked position.

As shown in FIG. 15B, the biasing member 238 is expanded toward its non-bent position. Since the slot 234 has a width that is smaller than the diameter of the needle body 136, movement of the needle is prevented and the needle tip 136a therefore cannot be pushed to extend outside the safety guard 210. The guidewire 59 that is disposed within the bore of the needle body 136 can, however, pass through the slot 234 because the slot has a width that is larger than the diameter of the guidewire. Thus, the biasing member 238 positions the slot 234 to permit the guidewire to exit the safety cap 216 even when the pivotable latch 222 is canted about the needle body. Moreover, advancement of the wire does not restrict the latch from being canted.

In view of the above, the catheter insertion apparatus of the present disclosure is therefore operable to provide the following: 1) blood flash visibility flash through the catheter; 2) blood flash visibility in the wire tube before guidewire advancement, including the ability to re-confirm flash if stopped; 3) blood flash visibility in the wire tube during wire advancement, including the ability to re-confirm flash if stopped; 4) blood flash visibility in the wire tube after wire advancement, including the ability to re-confirm flash if stopped; 5) the wire tip is located inside the needle and near the needle tip during the start of the catheterization procedure; and 6) the wire tube design prevents excessive blood exposure and separates the blood in the wire tube from the wire in wire tube.

While the catheter insertion apparatus has been described in terms of what may be considered to be specific aspects, the present disclosure is not limited to the disclosed aspects. Additional modifications and improvements to the catheter insertion apparatus may be apparent to those skilled in the art. Moreover, the many features and advantages of the disclosure are apparent from the detailed specification, and thus, it is intended by the appended claims to cover all such features and advantages of the disclosure which fall within the spirit and scope of the disclosure. Further, it is not desired to limit the disclosure to the exact construction and operation illustrated and described, and accordingly, all suitable modifications and equivalents may be resorted to, falling within the scope of the disclosure. Accordingly, the present disclosure should be considered as illustrative and not restrictive. As such, this disclosure is intended to cover various modifications and similar arrangements included within the spirit and scope of the claims, which should be accorded their broadest interpretation so as to encompass all such modifications and similar structures.

What is claimed is:

1. A catheter insertion apparatus, comprising:
    a needle including a needle body connected to a needle hub, the needle body having a longitudinal bore and a distal needle tip configured to pierce a wall of a blood vessel, and the needle hub having an internal flow passage in fluid communication with the longitudinal bore of the needle body;
    a catheter configured to removably fit over the needle body, the catheter including a catheter body connected to a catheter hub;
    a housing including an elongated housing body connected to the needle hub, the elongated housing body having a longitudinal guidewire track and an elongated lumen in fluid communication with the internal flow passage of the needle hub;
    a guide assembly slidably mounted to the elongated housing body and including a guidewire having a distal guidewire tip, the guide assembly configured to cooperate with the guidewire track, and the guidewire operable to move between a retracted position in which the distal guidewire tip is located within the needle body and an extended position in which the distal guidewire tip is located outside of the needle body;
    a continuous flashback chamber defined by the elongated lumen of the elongated housing body, the continuous flashback chamber configured to allow visualization of a continuous flow of blood during insertion of the distal needle tip into the blood vessel; and
    a flow diverter having a proximal end and a distal end, wherein the proximal end of the flow diverter is disposed within a distal end of the guidewire track and configured to restrict the continuous flow of blood from entering the guidewire track, and the distal end of the flow diverter is disposed in the needle hub and has a slanted surface configured to divert the continuous flow of blood from the internal flow passage of the needle hub into the continuous flashback chamber and away from the guidewire track.

2. The catheter insertion apparatus according to claim 1, wherein the continuous flashback chamber is operable to receive the continuous flow of blood during insertion of the distal needle tip into the blood vessel when the guidewire is in the retracted position, when the guidewire is in the extended position, and during movement of the guidewire between the retracted and extended positions.

3. The catheter insertion apparatus according to claim 2, wherein the guide assembly further comprises an actuator connected to a proximal end of the guidewire, the actuator being movable relative to the housing and the needle to correspondingly move the guidewire relative to the housing and the needle between the retracted and extended positions.

4. The catheter insertion apparatus according to claim 3, wherein the actuator includes a collar configured to slidably mount to the housing body.

5. The catheter insertion apparatus according to claim 4, wherein the actuator further includes a handle connected to the collar for manually sliding the collar along a longitudinal length of the housing body.

6. The catheter insertion apparatus according to claim 4, wherein the housing body further includes an annular band configured to abut the collar of the actuator when the guidewire is at the retracted position.

7. The catheter insertion apparatus according to claim 4, wherein the actuator further includes a slide member extending inwardly from the collar, the slide member having a neck portion and a head portion.

8. The catheter insertion apparatus according to claim 7, wherein the proximal end of the guidewire is connected to the head portion of the slide member.

9. The catheter insertion apparatus according to claim 7, wherein the longitudinal guidewire track is configured to slidably receive the head portion of the slide member.

10. The catheter insertion apparatus according to claim 7, wherein the housing body further comprises a longitudinal slot configured to slidably receive the neck portion of the slide member.

11. The catheter insertion apparatus according to claim 3, wherein the actuator further includes an indicator configured to line up with corresponding indicia disposed along the housing body to indicate a distance of guidewire movement into the blood vessel during an insertion procedure.

12. The catheter insertion apparatus according to claim 1, wherein the flow diverter includes a through-hole configured to slidably receive the guidewire.

13. The catheter insertion apparatus according to claim 1, wherein the flow diverter forms a seal with a portion of a distal end of the housing body that restricts the continuous flow of blood from leaking out of the housing.

14. The catheter insertion apparatus according to claim 1, wherein the housing body comprises a substantially crescent shaped cross-section.

15. The catheter insertion apparatus according to claim 1, wherein the housing body and the needle hub comprise a transparent material or a translucent material.

16. The catheter insertion apparatus according to claim 1, further comprising a quick flashback chamber configured to allow visualization of an initial flow of blood upon insertion of the distal needle tip into the blood vessel.

17. The catheter insertion apparatus according to claim 16, wherein the quick flashback chamber is defined between the needle body and the catheter body, and wherein the needle body includes a side port to direct the initial flow of blood into the quick flashback chamber.

18. The catheter insertion apparatus according to claim 1, further comprising a vent plug connected to a proximal end of the housing body and configured to prevent blood leakage from the lumen of the housing body.

19. The catheter insertion apparatus according to claim 1, wherein the needle hub further comprises a safety guard configured to provide sharps protection to the distal needle tip.

* * * * *